United States Patent [19]

Carroll et al.

[11] Patent Number: 5,186,848

[45] Date of Patent: * Feb. 16, 1993

[54] PREPARING SULFUR SOLVENT COMPOSITIONS COMPRISING TREATING A SULFIDE AND POLYALKYLENEOXYAMINE OR POLYALKYLENEOXYPOLYAMINE MIXTURE WITH AN ALKYLAMINE OR ALKANOLAMINE

[75] Inventors: Glenn T. Carroll, Jeffersonville; Michael J. Lindstrom, Downingtown, both of Pa.

[73] Assignee: Elf Atochem North America, Inc., Philadelphia, Pa.

[*] Notice: The portion of the term of this patent subsequent to Feb. 14, 2006 has been disclaimed.

[21] Appl. No.: 678,905

[22] Filed: Mar. 28, 1991

Related U.S. Application Data

[63] Continuation of Ser. No. 255,221, Oct. 11, 1988, abandoned.

[51] Int. Cl.⁵ ............................................. E21B 37/00
[52] U.S. Cl. ................................. 252/8.552; 252/364
[58] Field of Search .......................... 252/364, 8.552

[56] References Cited

U.S. PATENT DOCUMENTS

| | | | |
|---|---|---|---|
| 3,545,916 | 12/1970 | Deicher | 23/2 |
| 3,809,655 | 5/1974 | Williams | 252/391 |
| 3,846,311 | 11/1974 | Sharp et al. | 252/8.55 B |
| 4,033,410 | 7/1977 | Kauffman | 166/244 C |
| 4,239,630 | 12/1980 | Atkinson et al. | 252/8.55 B |
| 4,248,717 | 2/1981 | Sharp et al. | 252/8.55 B |
| 4,290,900 | 9/1981 | Sharp et al. | 252/8.55 B |
| 4,295,979 | 10/1981 | Sharp et al. | 252/8.55 E |
| 4,350,600 | 9/1982 | Sharp et al. | 252/8.55 E |
| 4,379,490 | 4/1983 | Sharp | 166/304 |
| 4,804,485 | 2/1989 | Carroll et al. | 252/8.552 |
| 5,028,343 | 7/1991 | Lindstrom | 252/8.552 |

FOREIGN PATENT DOCUMENTS

| | | |
|---|---|---|
| 974912 | 9/1975 | Canada . |
| 2579203 | 9/1986 | France . |
| 2579585 | 10/1986 | France . |

OTHER PUBLICATIONS

P. D. Clark et al. "The Composition of Merox–Oily Disulfide Mixtures" ASRL Quarterly Bul., vol. XVIII, Nos. 2, 3 and 4 (1982) pp. 44+.

P. D. Clark et al. "New Catalysts for Merox Solutions in Downhole Sulphur Plug Removals" ASRL Quarterly Bul., vol. XIX, Nos. 1 and 2 (1982) p. 4+.

*Primary Examiner*—Gary L. Geist

[57] ABSTRACT

A process is disclosed for preparing a composition having improved solvent power for sulfur wherein a composition comprising a sulfide having the general formula RSSaSR' wherein R and R' are defined carbon-containing radicals and a is 0 to 3, and a catalyst for improving the ability of said composition to take up sulfur is treated, either before, during or after the addition of said catalyst to said composition, with a primary or secondary amine in an effective amount and for an effective time period.

10 Claims, No Drawings

PREPARING SULFUR SOLVENT COMPOSITIONS COMPRISING TREATING A SULFIDE AND POLYALKYLENEOXYAMINE OR POLYALKYLENEOXYPOLYAMINE MIXTURE WITH AN ALKYLAMINE OR ALKANOLAMINE

This is a continuation of copending application Ser. No. 7/255,221 filed on Oct. 11, 1988 now abandoned.

BACKGROUND

This invention relates to a process for preparing catalyst containing, sulfur-solvent compositions wherein such compositions are treated, before, during or after incorporation of said catalysts, to inhibit the deleterious effects of impurities. More particularly, it relates to a process wherein sulfide-containing, sulfur solvents are treated with primary or secondary amines whereby the catalyst poisoning effects of impurities in the solvent are inhibited.

In the processing of sour gas wells, sulfur may form deposits that can plug the well and terminate production. These deposits have been prevented or minimized by flowing solvents such as carbon disulfide, organic solvents, and aqueous alkylamines (U.S. Pat. No. 3,545,916), downhole. The solvent is injected and the well is allowed to soak for a sufficient period of time to dissolve any existing sulfur plugs. Alternatively, the solvent can be injected continuously in amounts sufficient to prevent the formation of sulfur deposits.

Dialkyl disulfides, either alone or blended with dialkyl sulfides (U.S. Pat. No. 3,531,160), have become the sulfur solvents of choice. Hyne [Alberta Sulfur Research Ltd. (ASRL), Quarterly Bulletin, vol. XVIII, Nos. 2, 3, and 4, 1982, p. 44] has shown that lower dialkyl disulfides, especially dimethyl disulfide (DMDS) are preferred. Alone they take up only a limited amount of sulfur; however, in conjunction with a suitable catalyst system, they will take up approximately 1.5 times their weight in sulfur at room temperature.

Impurities which may occur in the sulfide-catalyst compositions referred to above will poison the catalyst and prevent it from improving the ability of the composition to take up or dissolve sulfur. These impurities, including carbon disulfide and alkyl mercaptans, are formed within the dialkyl disulfide or polysulfide during manufacture. In addition, when these compositions are injected into a sour gas well they are exposed to impurities from the well gas stream which impurities, including carbon disulfide and carbon oxysulfide, are increased as the bottom-hole temperature and pressure increase (Hyne, J. B. et al., *World Oil*, 1980, October, 111). In wells which contain high amounts of carbon disulfide and carbon oxysulfide, the catalyst in the sulfide compositions may react with these impurities and become poisoned.

PRIOR ART

It is known to circulate liquid alkyl sulfides or disulfides in a sour gas well to dissolve and remove sulfur (U.S. Pat. No. 3,531,160). It is also known to catalyze a liquid (di)alkyl disulfide with various active compounds to substantially increase the sulfur take-up or solvent power of the sulfide chemical. The use of a saturated aliphatic amine as a catalyst for the liquid dialkyl disulfide has been found very effective particularly subsequent to aging the sulfide-catalyst composition (U.S. Pat. No. 3,846,311).

STATEMENT OF THE INVENTION

This invention is a process for preparing a liquid sulfur-solvent composition containing a major proportion of a sulfide or mixture of sulfides of the formula: $RSS_aSR'$ where R and R' are independently alkyl, alkaryl, alkoxyalkyl or hydroxyalkyl radicals having from 1 to 24 carbon atoms in the alkyl moieties, phenyl or alkyl substituted phenyl and the value of a is 0 to 3, and a catalyst for improving the ability of said composition to take up sulfur, said process comprising treating said composition, before, during or after the addition of said catalyst to said composition, with a primary or secondary amine in an effective amount and for an effective period of time.

DETAILED DESCRIPTION OF THE INVENTION

The liquid sulfur-solvent compositions of this invention will contain a major proportion of a sulfide (or mixture thereof) having the formula

$$RSS_aSR'$$

where R and R' are independently alkyl, alkaryl, alkoxyalkyl or hydroxyalkyl radicals having from 1 to 24, preferably from 1 to 8 carbon atoms in the alkyl moiety, phenyl or $C_1$–$C_{20}$ alkyl substituted phenyl. Examples of these substituents include, methyl, ethyl, propyl, butyl, isobutyl, hexyl, octyl, isooctyl, decyl, dodecyl, octadecyl, phenyl, tolyl, xylyl and the like.

The value of a in the above formula is from 0 to 3 and, in a mixture of such sulfides, represents the average number of internal sulfurs and not the maximum number of sulfurs for any one species in the mixture.

The catalysts for the sulfur-solvent composition include the catalysts mentioned in the prior art as useful for improving the sulfur uptake capacity of the sulfide and those disclosed in copending, coassigned application Ser. No. 047,956 now U.S. Pat. No. 4,804,985 and Ser. No. 047,955 now abandoned, each filed on May 8, 1987 and claiming, respectively, the use of polyalkyleneoxyamines or poly-amines and a mixture of a basic nitrogen-containing compound with an alcoholic or aqueous solution of an alkali hydroxide, alkoxide or carbonate. Examples of catalysts disclosed in the prior art are the unsubstituted, saturated amines, fatty acid amines, sodium hydrosulfide-dimethyl-formamide cosolvent, alkali salts of thiophenols-dimethyl-formamide cosolvent. Example of catalysts of the afore-mentioned copending applications are combinations of basic nitrogen-containing compounds including, for example, ammonia, aliphatic, amines, aryl amines, alkaryl amines, poly(alkyleneoxy)alkanolamines and their respective ethers, polyalkyleneoxyamines and polyamines, amides, sulfenamides, imines, and enamines, and alcoholic or aqueous solution of alkali hydroxide or alkoxide, for example, sodium or potassium hydroxide or alkoxide. The catalyst of the copending applications include polyalkyleneoxyamines and polyamines containing a primary or secondary amine functionality and wherein the alkylene radical is a substituted or unsubstituted radical having 2 to 4 carbon atoms exclusive of substituent groups. Further examples of these amines are identified under formulas 1, 2, 3 and 4 of copending application Ser. No. 047,955 and Ser. No. 047,956 filed May 8, 1987.

The catalysts of the process of this invention are used in the herein described sulfide-catalyst compositions in amounts ranging from 0.05% up to about 10% based on the weight of the composition.

Examples of the amines which will inhibit the catalyst poisoning capability of impurities in the composition include compounds of the formulae:

$$HNR^1R^2 \qquad A)$$

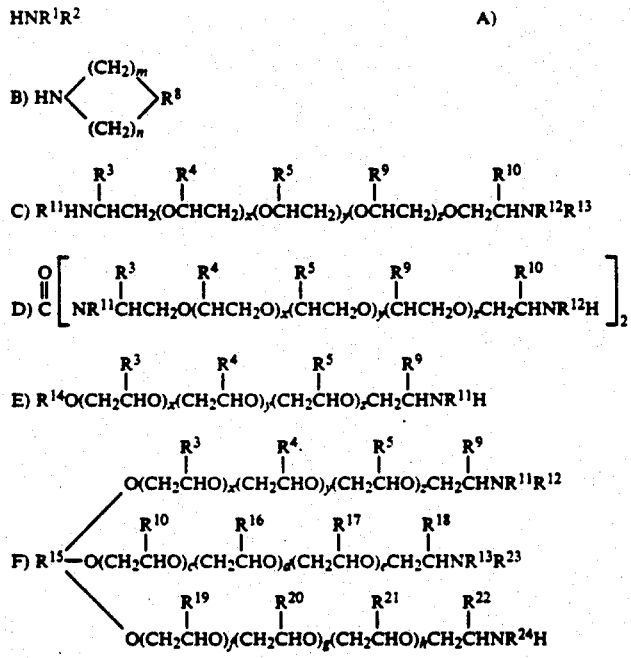

where $R^1$ and $R^2$ are independently H, alkyl, alkaryl, hydroxyalkyl, alkoxyalkyl wherein the alkyl moieties have from 1 to 20, preferably 1 to 6 carbon atoms, aryl or $R^6$ where

and $R^3$, $R^4$, $R^5$, $R^7$, $R^9$, $R^{10}$, $R^{14}$, $R^{16}$, $R^{17}$, $R^{18}$, $R^{19}$, $R^{20}$, $R^{21}$, and $R^{22}$ are independently H, alkyl, alkaryl, hydroxyalkyl, alkoxyalkyl, haloalkyl wherein the alkyl moieties have from 1 to 20, preferably 1 to 6 carbon atoms, or phenyl; $R^8$ is $CH_2$, O, S, or $NR^1$; $R^{11}$, $R^{12}$, $R^{13}$, $R^{23}$, and $R^{24}$ are independently H, alkyl and alkaryl wherein the alkyl moieties have from 1 to 10 carbon atoms, aryl, or $CONH_2$; $R^{15}$ is the hydrocarbon residue of a triol; m and n are independently integers of from 1 to 6, and c, d, e, f, g, h, x, y, and z are independently integers of from 0–200 provided, however, that the total of such integers equal at least 2.

Formulas A–F, shown above, are given as examples of the primary or secondary amines useful as inhibitors of sulfide impurities for this invention. Any compound having a primary or secondary amine functionality, including those disclosed above as catalysts, are effective.

The preferred primary (p-) or secondary (sec-) amines used for the treatment procedure of this invention include the alkylamines and alkanolamines represented by the above formula A. More preferably, the p- and sec-amines are alkyl and alkanolamines having from 1 to 6 carbon atoms in the alkyl moieties; most preferably, ethylamine or ethanolamine are used. Also included as preferred p- or sec-amines are the polyalkyleneoxyamines or polyamines represented by the previously described formulae A where $R^1$ and $R^2 = R^6$, C, D, E, and F, particularly Jeffamine® D230, a polyalkyleneoxypolyamine sold by Texaco Chemical Company and having the formula:

where x is 2.6.

The amounts of the p- or sec-amines used to inhibit deleterious effects of impurities will depend on the concentration of such impurities in the composition. Accordingly, the p- or sec-amines will be used in amounts sufficient to inhibit the catalyst poisoning effects of impurities in the compositions. Amounts of 0.05% and less, based on the sulfide in the composition are useful. However, the preferred amounts will range from about 0.1 to 10% based on the weight of the sulfide in the composition, most preferably, from 0.1 to about 1%.

The sulfide is treated with the amine for a period of time, at the temperature employed, sufficient to inhibit the deleterious effects of impurities in the sulfide. Generally, from a few minutes to many hours will be useful treatment periods. Preferably, the sulfide is treated with the amine for a time period ranging from about 20 minutes to about 72 hours.

The temperature at which the sulfide is treated with the amine for any specified period of time is that sufficient to inhibit the deleterious effects of impurities in the sulfide. The temperature will range from room temperature and below up to just below the boiling point of the composition. Preferably, the treatment temperature ranges from about 25° to about 80° C. applied within the preferred time period stated above.

The p- or sec-amine is used to treat the sulfur-solvent composition either before, during or after the addition of the catalyst system but preferably before. When utilizing catalyst compositions which are p- or sec-amines, an additional amount of such catalyst, sufficient to overcome the deleterious effects of the impurities in the sulfide, may be added to the catalytic amount of such catalyst composition and the combined amount added to the sulfide. It is more economical, however, to first treat the sulfide with an inexpensive amine to counter the deleterious effects of the impurities followed by the addition of a generally more expensive catalyst system.

The following examples are set forth to demonstrate this invention.

EXAMPLE 1

A composition of 9.5 g of dimethyl disulfide, which contained approximately 0.5% carbon disulfide and 0.05% methyl mercaptan as determined by vapor phase chromatography, 60 microliters (μl) Jeffamine ® ED-600* and 6.5 μl of dimethylaminoethanol was allowed to stand at room temperature for 4 hours. The composition was then bubbled with H$_2$S for 3 minutes, whereupon 3.5 g of sulfur were added. A time of 6.08 minutes was noted for the dissolution of the sulfur.

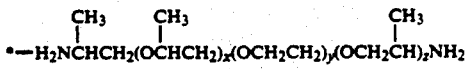

where $x+z=2.5$ and $y=8.5$.

EXAMPLE 2

A composition identical to that in Example 1, except that the dimethyl disulfide was treated with 0.1 wt % ethanolamine and allowed to stir for 25 minutes prior to the addition of the Jeffamine ® ED-600 and the dimethylaminoethanol, was bubbled with H$_2$S for 3 minutes after the composition stood for approximately 16 hours at room temperature. Sulfur (3.5 g) was then added and a time of 0.7 minutes was noted for its dissolution, thereby showing the effectiveness of said amine treatment process. Since the deactivation of the composition is caused by a reaction between the impurity and the catalyst, Jeffamine ® ED-600, the composition was allowed to set for 16 hours instead of four to further show the effectiveness of the disclosed treatment process.

EXAMPLE 3

A composition of 9.5 g of dimethyl disulfide, which contained no carbon disulfide and methyl mercaptan as determined by vapor phase chromatography and 40 μl Jeffamine ® ED-600 was bubbled with H$_2$S for 3 minutes, whereupon 3.5 g of sulfur were added. A time period of 0.68 minutes was noted for the dissolution of the sulfur showing that the decreased time in Example 2 was not caused simply by the addition of extra amine. Additionally, a lesser amount of catalyst, Jeffamine ® ED-600, and dimethyl-aminoethanol, were used, thereby providing additional proof that the lower time periods were not caused by adding additional amine.

We claim:

1. A process for preparing a liquid sulfur-solvent composition containing a major proportion of a sulfide or mixture of sulfides having the formula RSS$_a$SR$^1$ where R and R$^1$ are independently alkyl, alkaryl, alkoxyalkyl or hydroxyalkyl radicals having from 1 to 24 carbon atoms in the alkyl moieties, phenyl or C$_1$-C$_{20}$ alkyl substituted phenyl and the value of a is 0 to 3, and a catalyst which is a polyalkyleneoxyamine or polyalkyleneoxypolyamine, said process comprising treating said composition either before, during or after the addition of said catalyst to said composition, with a primary or secondary amine which is an alkylamine or alkanolamine or mixture thereof having alkyl moieties of from 1 to 20 carbon atoms, in an effective amount and for an effective period of time to inhibit the deleterious effects of impurities in said composition.

2. The process of claim 1 wherein said primary or secondary amine is an alkylamine or alkanolamine having alkyl moieties of from 1 to 6 carbon atoms.

3. The process of claim 1 wherein said composition is treated with said primary or secondary amine for a period of time ranging from 20 minutes to about 72 hours.

4. The process of claim 1 wherein the composition is treated at a temperature of from about 25° to about 80° C.

5. The process of claim 1 wherein said composition is treated with said primary or secondary amine before the addition of said catalyst.

6. The process of claim 1 wherein the amount of primary or secondary amine ranges from 0.1 to 10% based on the weight of the sulfide in said composition.

7. The process of claim 1 wherein said sulfide is dimethyl disulfide, dimethyl polysulfide or a mixture thereof.

8. The process of claim 7 wherein said primary or secondary amine is ethylamine or ethanolamine.

9. The process of claim 8 wherein said ethylamine or ethanolamine is used to treat the composition in an amount ranging from 0.1 to about 1%, based on the weight of the sulfide in the composition, and the temperature at which said composition is treated ranges from about 25° to about 80° C.

10. The process of claim 9 wherein said polyalkyleneoxyamine or polyalkyleneoxypolyamine is used to treat the composition in an amount ranging from 0.1 to about 1% based on the weight of the sulfide in the composition.